United States Patent
Belongia

(10) Patent No.: US 10,086,102 B2
(45) Date of Patent: Oct. 2, 2018

(54) WAX WARMER

(71) Applicant: S.C. Johnson & Son, Inc., Racine, WI (US)

(72) Inventor: David C. Belongia, Burlington, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 416 days.

(21) Appl. No.: 14/136,201

(22) Filed: Dec. 20, 2013

(65) Prior Publication Data

US 2015/0174278 A1  Jun. 25, 2015

(51) Int. Cl.
  *A61L 9/03* (2006.01)
  *H05B 3/78* (2006.01)

(52) U.S. Cl.
  CPC .................. *A61L 9/03* (2013.01); *H05B 3/78* (2013.01); *A61L 2209/135* (2013.01)

(58) Field of Classification Search
  CPC ... A61L 9/02; A61L 9/03; A61L 9/037; A61L 9/12; H05B 3/20
  USPC ........ 392/386, 391, 395, 390; 219/433, 438, 219/520, 536, 528
  See application file for complete search history.

(56) References Cited

U.S. PATENT DOCUMENTS

| 2,685,020 | A |   | 7/1954 | Laibow |
| 4,731,522 | A |   | 3/1988 | Manchester |
| 5,012,393 | A | * | 4/1991 | Knipe ..................... C03B 33/14 225/96 |
| 5,194,717 | A | * | 3/1993 | Cowen .................... F04C 29/04 219/201 |
| 5,448,449 | A |   | 9/1995 | Bright et al. |
| 5,647,052 | A |   | 7/1997 | Patel et al. |
| 5,922,231 | A |   | 7/1999 | Karst et al. |
| 6,251,481 | B1 |  | 6/2001 | Elmore |
| 6,412,670 | B1 |  | 7/2002 | Randmae et al. |
| 6,756,567 | B1 |  | 6/2004 | Suen |
| 6,765,797 | B2 |  | 7/2004 | Summers et al. |
| 7,046,919 | B2 | * | 5/2006 | Shimizu ................... A61L 9/03 392/390 |
| 7,059,795 | B2 |  | 6/2006 | Guillaume et al. |
| 7,132,084 | B1 |  | 11/2006 | Roumpos |

(Continued)

FOREIGN PATENT DOCUMENTS

| CN | 2766847 Y | 3/2006 |
| CN | 2917655 Y | 7/2007 |

(Continued)

OTHER PUBLICATIONS

PCT/US2014/070860 International Search Report and Written Opinion dated Oct. 5, 2015.

(Continued)

*Primary Examiner* — Dana Ross
*Assistant Examiner* — Ayub Maye
(74) *Attorney, Agent, or Firm* — Quarles & Brady LLP

(57) ABSTRACT

A wax warmer includes a body, a reservoir, and a plate. The reservoir is adapted to receive a wax melt. The plate is disposed adjacent to the body and the reservoir. A first surface of the plate is in thermal communication with the reservoir. A retention bracket is provided on a second surface of the plate. A threaded shaft extends from an outside surface of the retention bracket toward the interior of the body.

17 Claims, 10 Drawing Sheets

(56) References Cited

U.S. PATENT DOCUMENTS

| | | |
|---|---|---|
| 7,133,605 B2 | 11/2006 | Niemeyer |
| 7,252,805 B2 | 8/2007 | Hart et al. |
| 7,329,839 B2 | 2/2008 | Palmer |
| 7,481,571 B2 * | 1/2009 | Bistritzky ............ A01M 1/2033 362/253 |
| 8,192,041 B2 | 6/2012 | Hsiao |
| 8,364,028 B1 | 1/2013 | Vaske et al. |
| 2005/0016985 A1 | 1/2005 | Haas et al. |
| 2005/0150886 A1 * | 7/2005 | Niemeyer ................ A61L 9/03 219/385 |
| 2006/0163240 A1 | 7/2006 | Xiao |
| 2007/0031298 A1 | 2/2007 | Roumpos et al. |
| 2008/0116197 A1 * | 5/2008 | Penman .................... A61L 9/03 219/526 |
| 2010/0096376 A1 | 4/2010 | Hsiao |
| 2011/0110072 A1 | 5/2011 | Hsiao |
| 2011/0110824 A1 * | 5/2011 | Hsiao ...................... A61L 9/035 422/125 |
| 2012/0024837 A1 * | 2/2012 | Thompson ................ A61L 9/03 219/433 |
| 2012/0183280 A1 | 7/2012 | Kowalec et al. |
| 2012/0318779 A1 | 12/2012 | Juarez |
| 2013/0020307 A1 | 1/2013 | Ashton et al. |
| 2013/0170184 A1 | 7/2013 | Browder et al. |

FOREIGN PATENT DOCUMENTS

| | | |
|---|---|---|
| CN | 201227432 Y | 4/2009 |
| CN | 202349885 U | 7/2012 |

OTHER PUBLICATIONS

First Office Action issued for Chinese Application No. 201480073240.2, dated Apr. 4, 2018, 14 pages.

* cited by examiner

WAX WARMER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure generally relates to a wax warmer, and more specifically, to a wax warmer for use with a wax melt to dispense materials into the surrounding environment.

2. Description of the Background of the Invention

Candles have been used for centuries to provide illumination and pleasant aromas to the surrounding environment. At its most basic level, a candle consists of a wick dipped in wax. The wick is lit and provides light while the burning or melting wax may provide a pleasant aroma. Alternatively, unscented or scented candles or wax melts can be placed in a warmer. These candles or warmers may also be used to provide more than just illumination and/or pleasant fragrances. For instance, candles and warmers may be placed outside around a patio or deck. The wax or oil may include materials with insect repellant properties along with providing a pleasant aroma and/or illumination. Generally, users can burn or warm waxes and oils to provide desired effects to the surrounding atmosphere or environment.

Traditional warmers and candles may have some drawbacks. Candles may be forgotten and left unsupervised and may represent a fire hazard. Also, a candle flame may be extinguished with a slight breeze or gust of wind. Melted wax may splatter or make a mess with traditional candles. An additional drawback associated with candles is the inability to control the intensity of the heat being provided to the scented material. A candle flame is not easily adjustable and thus the amount of heat the flame provides to the infused wax or oil does not allow a user to vary the strength of the fragrance introduced into the surrounding environment.

Some attempts have been made to overcome the aforementioned drawbacks associated with warmers and candles through the use of electric wax warmers. An electric wax warmer consists of a heater in thermal contact with a reservoir for holding a wax melt or infused oil. The heater replaces the candle in a traditional warmer and melts the wax or heats the oil in the reservoir resulting in the same benefits as previously mentioned. The lack of a flame reduces the risk associated with traditional warmers and candles. Another advantage may be the temperature of the heater in an electric wax warmer can be adjusted. This provides the user with more control over the amount of fragrant or other materials introduced into the surrounding environment. Electric wax warmers also have more consistent performance indoors and outdoors and are less messy than traditional candles and warmers.

Electric wax warmers may have significant advantages over traditional warmers and candles, however, they may also have some drawbacks. There are many different types of heaters that can be used in an electric wax warmer. Some examples include resistive, positive thermal coefficient, and inductive type heating elements. Many of the heating elements available are fragile and require careful handling to prevent damage during manufacturing and use. Besides being handled and secured to prevent damage, the heating element in an electric wax warmer needs to maintain a strong thermal contact with the reservoir. The amount of electricity needed during operation is reduced as the quality of the thermal contact improves. There are numerous examples in the art of very complex structures employed to safely position a heating element in thermal contact with a reservoir. However, complexity adds cost in materials and cost in manufacturing. In contrast, some of the simple heating element mounting means may not adequately protect the heating element and may result in manufacturing defects.

Therefore, there is a need for an electric wax warmer that overcomes the aforementioned drawbacks. In particular, there is a need for a wax warmer that provides superior thermal performance to a user while being cost effective for a user. Further, there is a need for a wax warmer that provides an easy and efficient means for mounting and maintaining a heating element in thermal contact with a reservoir containing a wax melt. Further still, there is a need for a wax warmer that is easy to manufacture to keep manufacturing costs down and prevent manufacturing defects. There is also a need for a wax warmer that is made from low cost materials while delivering improved performance.

The present disclosure overcomes some of the aforementioned drawbacks by providing a wax warmer that maintains excellent thermal contact between the heating element and the reservoir. The wax warmer disclosed herein also minimizes the material and manufacturing costs and reduces the opportunity to damage the heating element during assembly.

SUMMARY OF THE INVENTION

According to one aspect, a wax warmer includes a body, a reservoir, and a plate. The reservoir is adapted to receive a wax melt. The plate is disposed adjacent to the body and the reservoir. A first surface of the plate is in thermal communication with the reservoir. A retention bracket is provided on a second surface of the plate. A threaded shaft extends from an outside surface of the retention bracket toward the interior of the body.

According to another aspect, a heater assembly for a wax warmer includes a heater and a resilient heater clip. The resilient heater clip includes at least two contact portions with the heater. The portion of the resilient heater clip between the at least two contact portions is not in contact with the heater.

According to a further aspect, a heater assembly for a wax warmer includes a heater and a resilient heater clip. The resilient heater clip is provided with a non-uniformly planar shape having a straight line length L between opposing distal ends thereof. A ratio of the length L and a total length T of the resilient heater clip is between about 0.5 to about 0.95.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Figure 1:
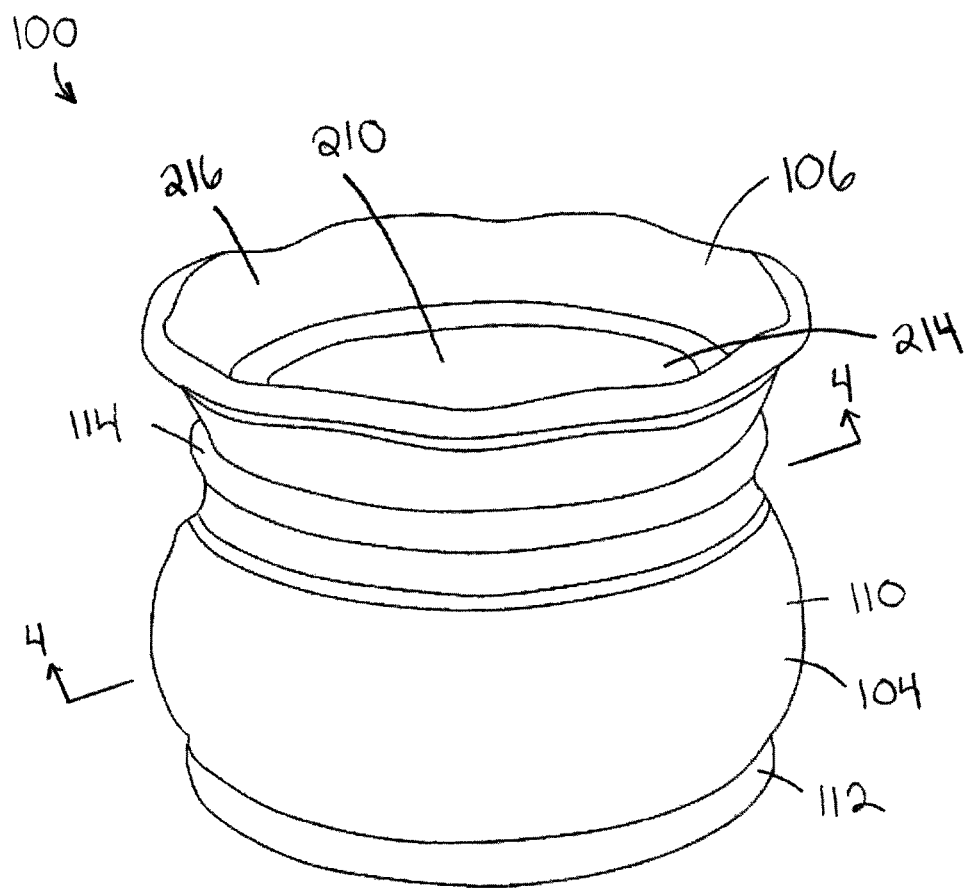
FIG. 1 is a perspective view of a wax warmer.
Figure 2:
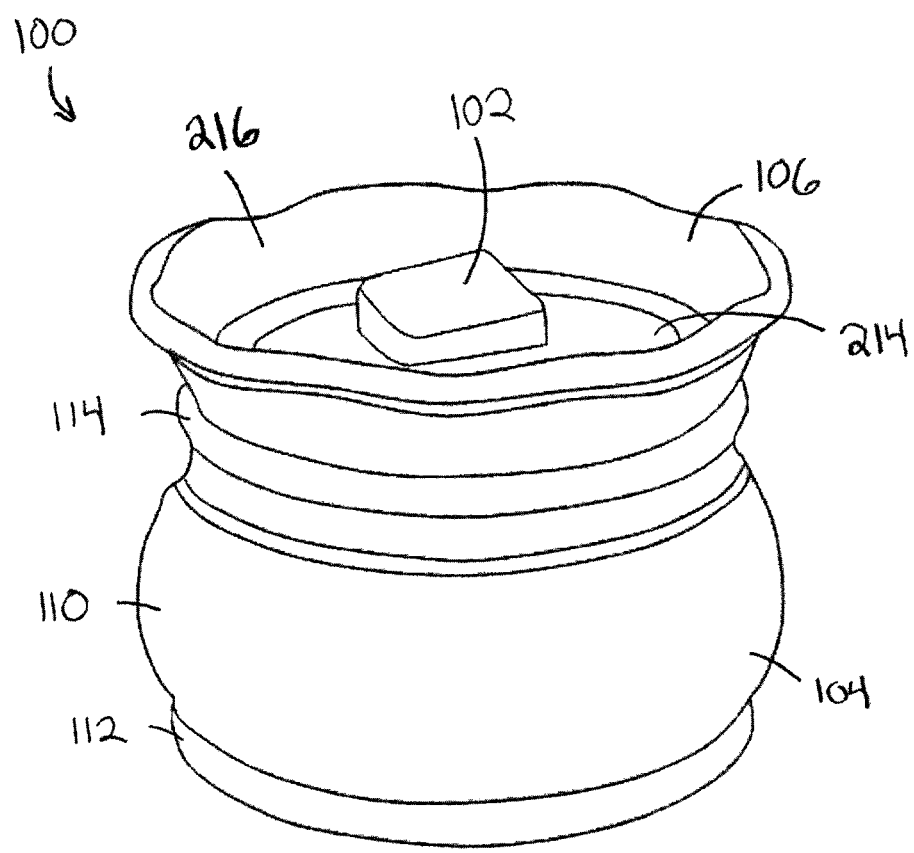
FIG. 2 is a perspective view of a wax warmer with a wax melt.

Referring to FIGS. 1-4, a wax warmer 100 is depicted. The wax warmer 100 is designed to heat a wax melt 102 (see FIG. 2) and thereby release a fragrance or other material contained therein into the surrounding environment. The wax warmer 100 generally includes a body 104, a reservoir 106, and a heater assembly 108 (see FIGS. 3 and 4). The body 104 is fashioned to house the heater assembly 108 and provide a support structure for the reservoir 106. The wax warmer 100 is generally described to include the aforementioned components, but the wax warmer 100 may be adapted to add or remove various components according to specific user requirements.

Figure 4:
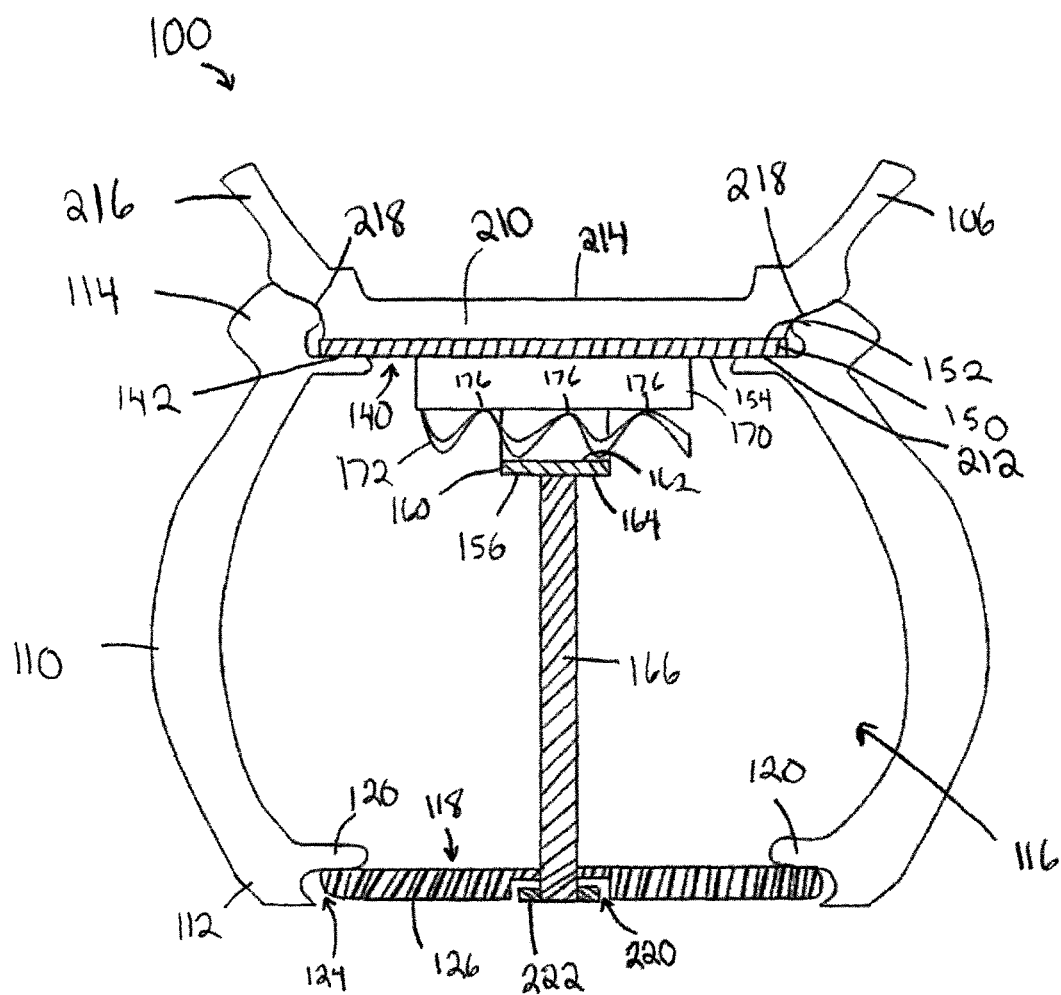
FIG. 4 is a cross-sectional view of a wax warmer taken generally along the line 4-4 of FIG. 1.
Figure 5:
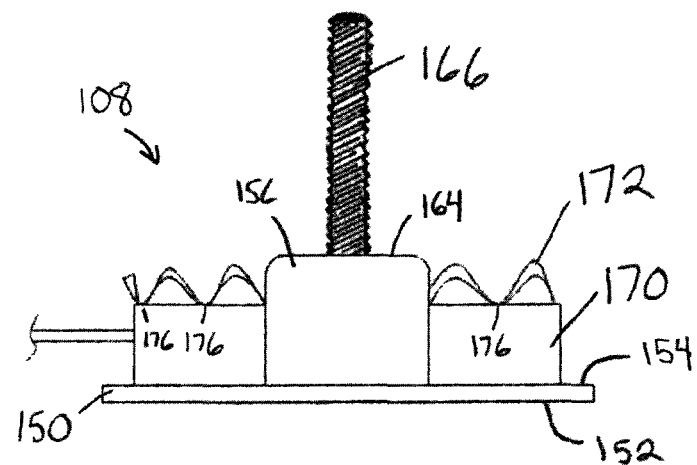
FIG. 5 is a front elevational view of a heater assembly.
Figure 6:
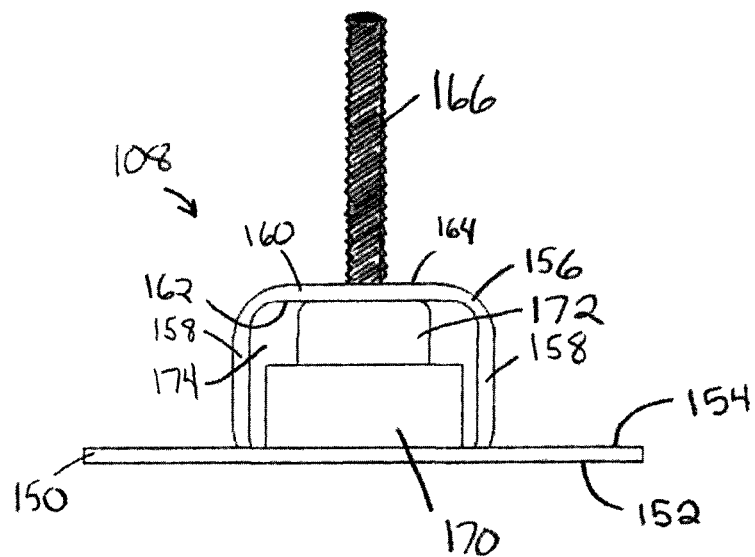
FIG. 6 is a side elevational view of the heater assembly of FIG. 5.

With respect to FIG. 4, the body 104 includes a sidewall 110 having a bottom end 112 and a top end 114. In the present embodiment, the sidewall 110 is generally cylindrical in shape and defines an inner space 116. The bottom end 112 defines a first opening 118. A lip 120 extends from an inner surface 122 of the sidewall 110. The bottom end 112 and the lip 120 form a recess 124 adapted to receive a base plate 126. The base plate 126 may include extensions (not shown) or other structures (feet, pads, structures with high coefficients of friction, etc.) generally know to those having ordinary skill in the art to provide stability to the wax warmer 100.

Figure 3:
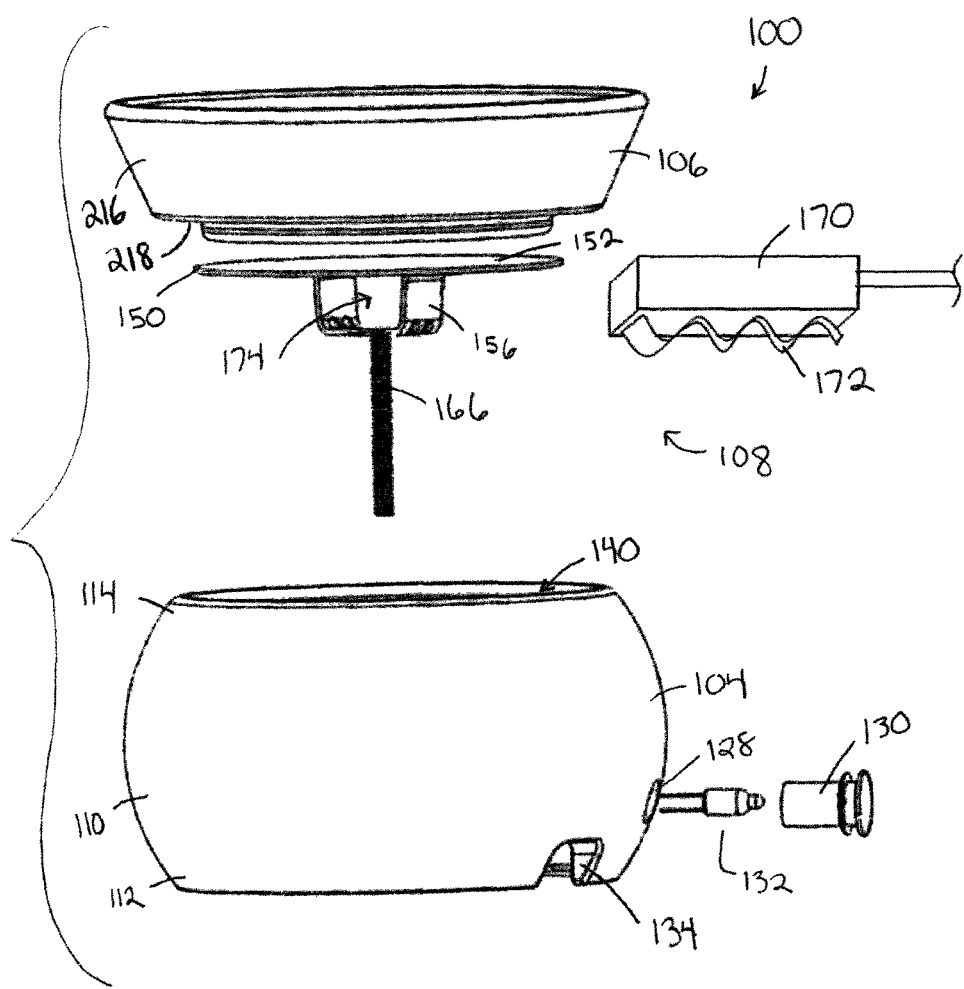
FIG. 3 is a exploded view of a wax warmer.

The bottom end 112 further includes a first aperture 128 provided in the sidewall 110 (see FIG. 3). The aperture 128 is adapted to receive an indicator cover 130. The indicator cover 130 is further adapted to receive an indicator 132. Preferably, the indicator 132 is a light, e.g., a light emitting diode. However, the indicator 132 may comprise any form of visual indication means known to those of ordinary skill in the art. A second aperture 134 is also provided proximal to the bottom end 112 of the sidewall 110. Preferably, the second aperture 134 provides a pass-through for an electrical cord (not shown) in electrical communication with the indicator 132 and the heater assembly 108.

Turning again to FIG. 4, a second opening 140 is defined by the top end 114 of the sidewall 110. The second opening 140 includes a shoulder 142 extending radially inwardly from the inner surface 122 of the sidewall 110. The second opening 140 and the shoulder 142 are adapted to receive the heater assembly 108 and the reservoir 106.

It has been contemplated that the body 104 and the reservoir 106 are preferably made from a ceramic material. However, any other materials as known to those having ordinary skill in the art may be used, such as plastic, metal, stone or other natural materials, etc. The body 104 and the reservoir 106 may take any geometric shape, e.g. a square, to provide different appearances. Further, the exterior surfaces of the body 104 and the reservoir 106 may be provided with any type of surface indicia, raised patterns, or any other decorations to configure the wax warmer 100 for aesthetic purposes.

Referring to FIGS. 3-7, the heater assembly 108 includes a plate 150 having a first surface 152 and a second surface 154. A retention bracket 156 is provided on the second surface 154 of the plate 150. The retention bracket 156 includes vertical members 158 and a horizontal member 160 (see FIG. 6). In the present embodiment, the retention bracket 156 is substantially U-shaped with the open end of the U attached to the second surface 154 of the plate 150. The horizontal member 160 of the retention bracket 156 includes a first side 162 and a second side 164. A threaded rod 166 is provided on the second side 164 of the horizontal member 160 of the retention bracket 156. A heater 170 and a resilient heater clip 172 are provided within an aperture 174 of the retention bracket 156. Preferably, the resilient heater clip 172 is sized to be compressed slightly when disposed between the horizontal member 160 of the retention bracket 156 and the heater 170. The compression of the resilient heater clip 172 forces the heater 170 to remain firmly in contact with the second surface 154 of the plate 150. This arrangement of the resilient heater clip 172, the heater 170, and the plate 150 results in good thermal contact between the aforementioned structure during operation of the wax warmer 100.

In a preferred embodiment, the threaded rod 166 may be welded to the second side 164 of the horizontal member 160. It is contemplated that the threaded rod may be attached to the second side 164 of the horizontal member 160 by any means known to those of ordinary skill in the art. For example, the threaded rod 166 may also be glued, retained with a captured nut welded to the second surface 164, or integrally formed with the horizontal member 160. This arrangement is advantageous over the prior art in that the threaded rod 166 is not in direct contact with the heater 170, thereby preventing the common manufacturing defect of over tightening the rod 166 and cracking the heater 170. Further, the heat transfer down the rod 166 is greatly reduced over the prior art so as to reduce the need for insulating caps or materials to be placed on the end of the rod.

In the present embodiment the resilient heater clip 172 is depicted with a wave-like shape. The resilient heater clip 172 includes multiple points of contact 176 with the surface of heater 170. Preferably, by including multiple points of contact 176 between the heater 170 and the resilient heater clip 172, the force from the compression of the resilient heater clip 172 is spread out over the surface of the heater 170. The present embodiment also maintains the thermal contact between the heater 170 and the plate 150. Further, this arrangement of the heater 170 and the resilient heater clip 172 is easy to assemble in a manufacturing environment.

Figure 7:
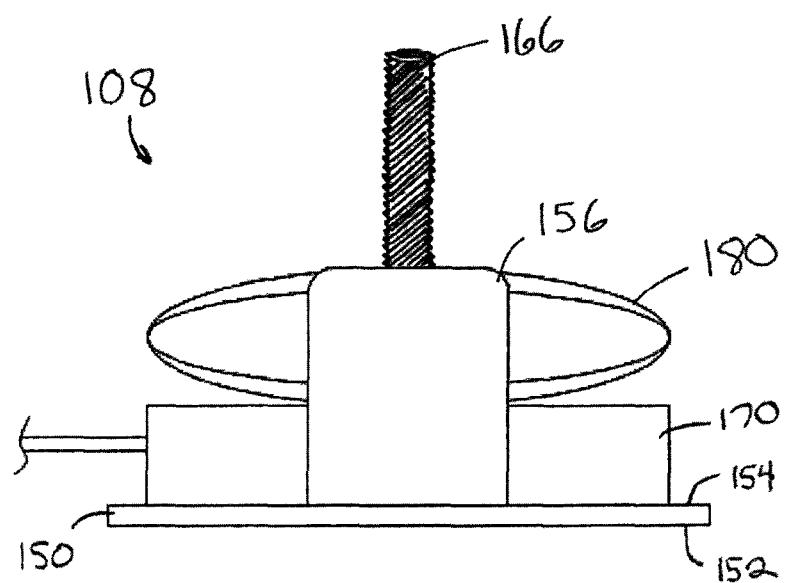
FIG. 7 is a side elevational view of a heater assembly including a second embodiment of a resilient heater clip.

Referring to FIG. 7, the heater assembly 108 includes a different embodiment of a resilient heater clip 180. The resilient heater clip 180 is substantially in the shape of an oval and placed between the heater 170 and the bracket 156 of the heater assembly 108. As with the resilient heater clip 172, the slight compression of the resilient heater clip 180 retains the heater within the bracket 156 and forces the heater 170 to maintain thermal contact with the second surface 154 of plate 150. It is contemplated that many different shapes and structures for the resilient heater clip 180 are possible by those with ordinary skill in the art.

Figure 8:
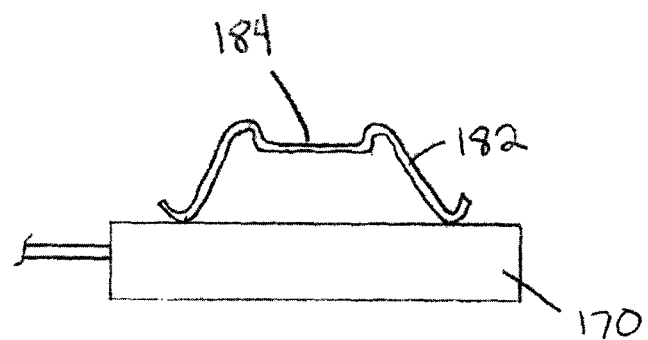
FIG. 8. is a side elevational view of a heater and a third embodiment of a resilient heater clip.

Now turning to FIG. 8, another embodiment of a resilient heater clip 182 is depicted on the heater 170. The resilient heater clip 182 includes a central recessed portion 184. The central recessed portion 184 is adapted to receive the horizontal member 160 of the retention bracket 156. The advantage of this structure is that the resilient heater clip locks into position with respect to the retention bracket 156. This aids in the assembly of the heater assembly 108 and makes the resilient heater clip self-centering with respect to the retention bracket 156. It is contemplated that the same effect of the recessed portion 184 may be achieved by welding or attaching tabs (not shown) to the resilient heater clip 182 instead of forming a recessed portion 184 by bending the material. Another alternative embodiment would be to weld or attach tabs (not shown) to the horizontal member 160, thereby creating a recessed portion (not shown) within the retention bracket 156 adapted to receive the resilient heater clip 182.

Figure 9:
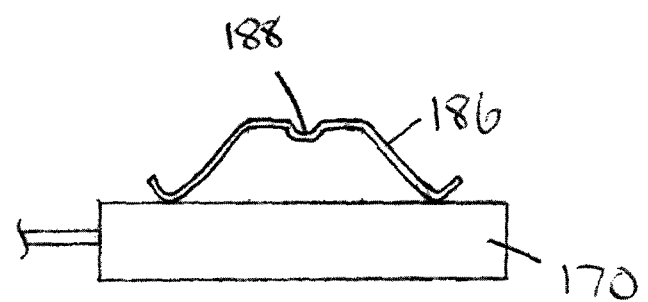
FIG. 9 is a side elevational view of a heater and a fourth embodiment of a resilient heater clip.

Now turning to FIG. 9, yet another embodiment of a resilient heater clip 186 is depicted on the heater 170. This embodiment of the resilient heater clip 186 includes a small, central recess 188 adapted to receive a detent (not shown) or protrusion (not shown) extending down from the horizontal member 160. Similar to the embodiment depicted in FIG. 8, the present embodiment may include multiple variations to accomplish similar self-centering and retention functions. For example, the central recess 188 may be a protrusion (not shown) adapted to be received in a recess (not shown) of the horizontal member 160 of the retention bracket 156.

Figure 10:
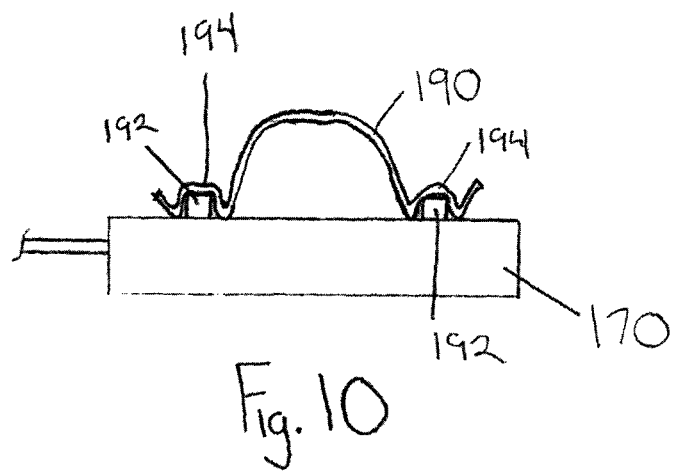
FIG. 10 is a side elevational view of a heater and a fifth embodiment of a resilient heater clip.
Figure 11:
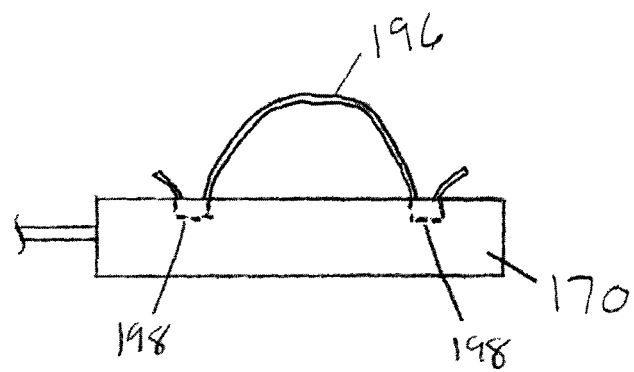
FIG. 11 is a side elevational view of a heater and a sixth embodiment of a resilient heater clip.

Now turning to FIG. 10, another embodiment of a resilient heater clip 190 is depicted on the heater 170. Ridges 192 are disposed on the heater 170. The resilient heater clip 190 includes end portions 194 adapted to receive the ridges 192. The retention of the ridges 192 within the end portions 194 maintains the location of the resilient heater clip 190 on the heater 170 during the assembly process. Now turning to FIG. 11, yet another embodiment of a resilient heater clip 196 is disposed on the heater 170. The heater 170 includes recessed portions 198 (shown with broken lines) adapted to receive the contact portions (unlabeled within the recessed portions 198). It is contemplated that one having ordinary skill in the art could design many variations of these advantageous structures to maintain the relationship between the heater 170 and the resilient heater clips 190, 196.

Figure 12:
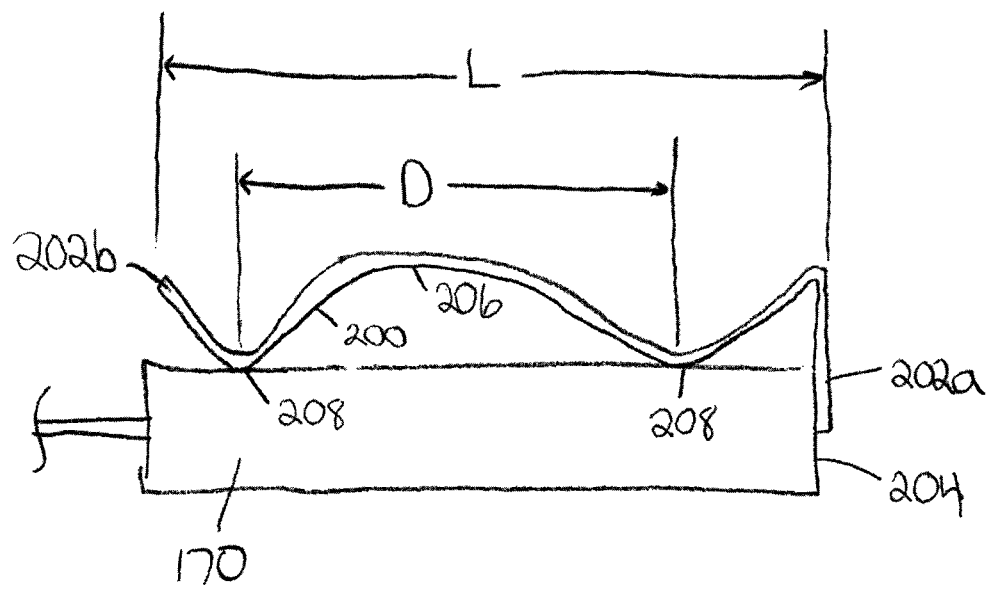
FIG. 12 is a side elevational view of a heater and a seventh embodiment of a resilient heater clip.

Now turning to FIG. 12, another embodiment of a resilient heater clip 200 is depicted on the heater 170, which may be generally characterized as being illustrative of the variations contemplated in connection with the clip. The resilient heater clip 200 includes opposing end portions 202a, 202b that may include a planar surface or an edge. In the present embodiment, 202a is represented by an elongate member disposed adjacent an end wall 204 of the heater 170. In the present embodiment, the end portion 202a assists in aligning the resilient heater clip 200 with respect to the heater 170 before being assembled into the heater assembly 108. In contrast, the end portion 202b is represented by an edge of a distal portion of the resilient heater clip 200.

The resilient heater clip 200 further includes an intermediate portion 206, which in the present embodiment may also be characterized as a medial portion. The intermediate portion 206 is generally characterized as a point of contact between the resilient heater clip 200 and the first side 162 of the retention bracket 156. In some embodiments, the intermediate portion 206 is a curved surface that contacts the bracket 156. In other embodiments, the intermediate portion 206 is a curved or angled surface that resiliently deforms from a first pre-operative state to a second operative state when it is in contact with the bracket 156, thereby deforming the intermediate portion 206 and providing a greater surface area in contact with the bracket 156. In other embodiments, the intermediate portion 206 is a flat or planar surface in contact with the bracket 156. In yet another embodiment, the intermediate portion comprises an angled surface. In fact, any geometric shape is contemplated. Further, it is also envisioned that multiple intermediate portions 206 may be provided for contact with the bracket 156, e.g., 2, 3, 4, 5, 6, or any number of intermediate portions. It is further contemplated that the intermediate portion 206 may include structural elements adapted to retain the resilient heater clip 200 and the heater 170 in the retention bracket 156. For example, the intermediate portion 206 may include a U-shaped indentation sized appropriately to receive the horizontal member 160 of the retention bracket 156 to prevent lateral movement of the resilient heater clip 182 and the heater 170 after assembly.

The resilient heater clip 200 also includes several heater contact portions 208, which may similarly comprise curved, angled, or planar sections as noted in connection with the intermediate portion 206. In fact, the contact portions 208 may also be provided with a curved or angled surface that resiliently deforms from a first pre-operative state to a second operative state when it is in contact with the heater 170. Further, other contact portions 208 may comprise other curved, angled, or flat surfaces that may be used to provide contact with the heater 170. It is also preferred that more than one contact portion 208 be provided, e.g., 2 contact portions, or 3, 4, 5, 6, or any number of contact portions. The utilization of additional contact portions 208 optimizes the transfer of force from the resilient heater clip 200 to the heater 170 to protect against breakage.

When the resilient heater clip 200 is assembled within the aperture 174 of the retention bracket 156, the intermediate portion(s) 206 is in contact with the first side 162 of the retention bracket 156. In turn, the force is transferred through the resilient heater clip 200 to the heater 170 at the contact portions 208. The distance between first and second contact portions may be generally described as D. Preferably, the distance D defines a void between opposing contact portions 208, i.e., an area and/or length where the resilient heater clip 200 does not contact the heater 170. In the instance where more than two contact portions 208 are provided, the distance D and D' may be identical or different, wherein each distance D and D' similarly defines a void. The overall shape of the resilient heater clip is of a non-uniformly planar structure, with a straight line length of the resilient heater clip 200 represented by a length L. The non-bent or total length of the resilient heater clip 200 is represented by a length T, wherein T>L. In a preferred embodiment, the ratio of L:T is between about 0.5 to about 0.95.

The resilient heater clips 172, 180, 182, 186, 190, 196, and 200 of the present embodiments may be constructed out of any appropriate material known to one having ordinary skill in the art. For example, spring steel that is ¾ or fully hardened is a material that exhibits the required resiliency properties at elevated temperatures. Some other examples may be brass, copper, or high temperature plastics and resins. It is also contemplated that the resilient heater clips 172, 180, 182, 186, 190, 196, and 200 may take on alternative forms of resilient members. For example, a wire spring or a coil spring may be modified by one having ordinary skill in the art to incorporate the features presented herein to achieve the desired benefits. It is also contemplated that the aforementioned resilient heater clips may be attached to the heater 170 or the retention bracket 156 by any number of means known to those of ordinary skill in the art. Some examples are welding, brazing, mechanical means such as rivets, nuts and bolts, screws, adhesives and resins, and tape.

In the preferred embodiment shown in the figures, the heater 170 is a resistive type heater. It is contemplated that the heater may be any type of heater known to those with ordinary skill in the art. For example, the heater may be a positive thermal coefficient heater or an inductive type heater. It is further contemplated that the heater 170 may be replaced by a series of heaters and resilient heater clips disposed on the second surface 154 of the plate 150.

Figure 13:
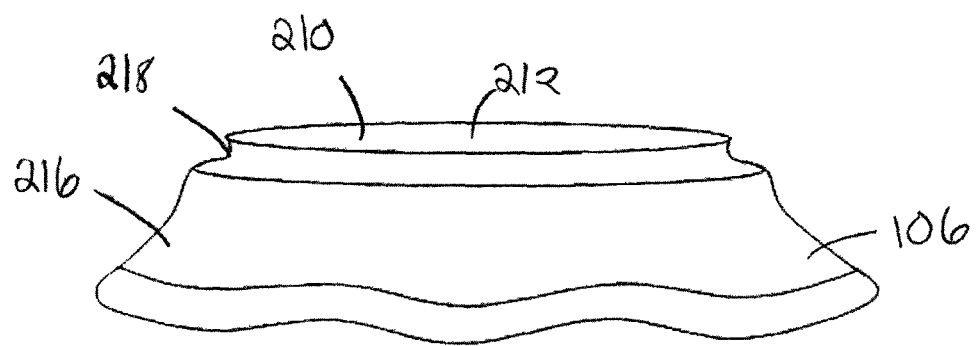
FIG. 13 is a bottom perspective view of a reservoir.

Turning to FIGS. 4 and 13, the reservoir 106 includes a bottom wall 210 having a first surface 212 and a second surface 214. The reservoir 106 further includes a sidewall 216. The bottom wall 210 and the sidewall 216 form a cup-like structure for containing the wax melt 102 in a pre-operative solid state and in an operative state when the wax melt 102 is in a liquid or semi-liquid state. The reservoir 106 further includes a cut-out 218. The shoulder 142 and the second opening 140 of the body 104 are configured to receive the plate 150 of the heating assembly 108 and the cut-out 218 of the reservoir 106. The first surface 212 of the reservoir 106 is generally flat to provide maximum thermal contact with the plate 150. The interaction of the cut-out 218 of the reservoir 106 and the shoulder 142 of the second opening 140 of the body 104 assists in retaining the reservoir 106 on the body 104. The present arrangement also ensures that the reservoir 106 is centered on the heater assembly 108 for improved thermal transfer from the heater 170 to the wax melt 102.

The wax warmer 100 in the embodiments depicted herein may be assembled quickly and efficiently. A wire harness (not shown) is first connected to the heater 170, the indicator 132, and an electrical power source (not shown). Preferably, the electrical power source is an electrical cord adapted to be plugged into an electrical socket. It is contemplated that the electrical power source may be batteries (not shown) contained within the body 104. It is further contemplated that any suitable electrical power source know to those having ordinary skill in the art may suffice. The next step in assembly is to insert the heater 170 and the resilient heater clip 172 into the retention bracket 156. The indicator 132 may then be inserted into the indicator cover 130. Next, the wire harness (not shown) and the heater assembly 108 may be inserted into the second opening 140. The threaded rod 166 is sized to extend through the interior space 116 of body 104 and through an opening 220 in base plate 126. A locking-nut 222 secures the threaded rod 166 to the base plate 126. In the preferred embodiment depicted herein, an electrical cord (not shown) extends through the second aperture 134. As depicted in FIG. 4, the assembled wax warmer 100 includes a reservoir in thermal contact with a plate 150. The plate 150 is in thermal contact with the heater 170. The heater 170 is retained within the bracket 156 by the compression of the resilient heater clip 172. The heater assembly 108 is retained within the second opening 140 of the body 104 by the threaded rod 166 extending through the base plate 126 and secured by the locking-nut 222.

The wax melt 102 is wickless and may comprise any geometric shape. In one preferred embodiment, the wax melt 102 has a generally square shape with slightly rounded curvature imparted thereto at an area where sidewalls of the wax melt intersect with each other. There are no substantial surface interruptions beyond minor surface irregularities formed during the manufacturing process. It is contemplated that the shape of the wax melt 102 may be configured to be beneficial for manufacturing purposes or aesthetic reasons or both.

Any of the embodiments described herein may be modified to include any of the structures or methodologies disclosed in connection with different embodiments. Further, the present disclosure is not limited to wax warmers of the type specifically shown. Still further, the wax warmers of any of the embodiments disclosed herein may be modified to work with any type of warmers that utilizes wax melts or the like.

INDUSTRIAL APPLICABILITY

A wax warmer is presented that heats a wax melt mixture for dispensing material into the surrounding environment. Thus, a user may experience the benefits provided by the material being introduced into the surrounding environment.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A wax warmer, comprising:
   a body;
   a reservoir configured to be supported by the body and receive a wax melt; and
   a heater assembly positioned within the body and in thermal contact with the reservoir, the heater assembly comprising:
      a heater; and
      a resilient heater clip, wherein compression of the resilient heater clip retains the heater within the heater assembly,
      wherein the resilient heater clip includes at least two contact portions with the heater, and
      wherein an intermediate portion of the resilient heater clip between the at least two contact portions is planar and not in contact with the heater.

2. The wax warmer of claim 1, wherein the resilient heater clip includes first, second, and third contact portions, and wherein the distance between the first and second contact portions is D and the distance between the second and third contact portions is D'.

3. The wax warmer of claim 1, wherein the heater is adjacent to a plate and the intermediate portion of the resilient heater clip is positioned between the heater and a portion of a bracket, wherein both the resilient heater clip and the heater are retained within the bracket.

4. The wax warmer of claim 1, wherein the resilient heater clip includes tabs adjacent the intermediate portion configured to lock the position of the resilient heater clip with respect to a bracket.

5. The wax warmer of claim 2, wherein D>D'.

6. The wax warmer of claim 2, wherein D=D'.

7. The wax warmer of claim 2, wherein the resilient heater clip includes at least four contact portions with the heater.

8. The wax warmer of claim 3, wherein the at least two contact portions are deformed upon placement within the bracket.

9. The wax warmer of claim 8, wherein the deformation of the at least two contact portions is elastic.

10. The wax warmer of claim 3, wherein the intermediate portion is in contact with the portion of the bracket.

11. The wax warmer of claim 10, wherein the at least one intermediate portion is deformed upon placement within the bracket.

12. A wax warmer, comprising:
a body;
a reservoir configured to be supported by the body and receive a wax melt; and
a heater assembly positioned within the body and in thermal contact with the reservoir, the heater assembly comprising:
a plate and a retention bracket provided thereon;
a heater; and
a resilient heater clip provided with a non-uniformly planar shape having a straight line length L between opposing distal ends thereof, wherein the resilient heater clip is disposed between the heater and the retention bracket, wherein a ratio of the length L and a total length T of the resilient heater clip is between about 0.5 to about 0.95, and wherein a first end portion of the resilient heater clip includes an elongate planar member that is adjacent an end wall of the heater.

13. The wax warmer of claim 12, wherein the heater and the resilient heater clip are retained within the retention bracket.

14. The wax warmer of claim 12, wherein the resilient heater clip includes at least one planar section intermediate the distal ends thereof.

15. The wax warmer of claim 12, wherein the resilient heater includes a plurality of curved or angled portions.

16. The wax warmer of claim 12, wherein a second end portion of the resilient heater clip extends away from a top surface of the heater adjacent a contact point on the top surface of the heater.

17. The wax warmer of claim 10, wherein the resilient heater clip includes tabs adjacent the intermediate portion configured to lock the intermediate portion into alignment with the portion of the bracket.

* * * * *